Figure 1:
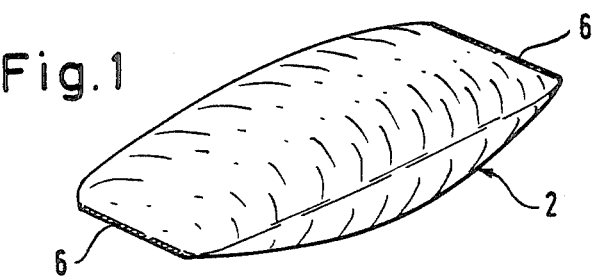

United States Patent [19]

Dahlke et al.

[11] Patent Number: 4,796,603

[45] Date of Patent: Jan. 10, 1989

[54] PAD-LIKE IMPLANT

[75] Inventors: Hermann Dahlke, Hamburg; Hans-Rainer Willmen, Grevenborich, both of Fed. Rep. of Germany

[73] Assignee: Ethicon, Inc., Somerville, N.J.

[21] Appl. No.: 92,908

[22] Filed: Sep. 4, 1987

[51] Int. Cl.⁴ .......................... A61B 19/00; A61F 2/02
[52] U.S. Cl. ................................. 128/899; 128/334 R; 623/11
[58] Field of Search ................... 128/1 R, 325, 334 R, 128/335.5; 623/11, 15, 16

[56] References Cited

U.S. PATENT DOCUMENTS

| | | | |
|---|---|---|---|
| 3,376,869 | 4/1968 | Borysko | 128/334 R |
| 3,739,773 | 6/1973 | Schmitt et al. | 128/334 R X |
| 3,875,928 | 4/1975 | Angelchik | 128/1 R |
| 3,937,223 | 2/1976 | Roth | 128/325 |
| 4,186,448 | 2/1980 | Brekke | 128/334 R X |
| 4,205,399 | 6/1980 | Shalaby et al. | 128/335.5 X |

Primary Examiner—Ronald L. Frinks

[57] ABSTRACT

The invention relates to a pad-like implant of resorbable material for the treatment of hernias, which comprises a cushion-like or hose-like body closed on all sides, whose outer sleeve comprises a knitted or woven hose of resorbable fibres or filaments or a perforated film of resorbable material, which is filled with a filling of threads, filaments, flocks or shreds of the same or a different resorbable material.

12 Claims, 1 Drawing Sheet

PAD-LIKE IMPLANT

The invention relates to a pad-like implant made from resorbable material for the treatment of hernias.

Implants for hernia treatment are known from U.S. Pat. No. 3,739,773, for example. They comprise flat or velour-like products, which are used in several layers or a spongy structure for the treatment of burns or other skin injuries and for numerous other purposes, as well as a pad material for hernias. Due to their porosity, they can absorb tissue fluid and are gradually permeated by bone substance or tissue which, following complete resorption of the implant, takes over its supporting or holding function.

However, such textile-like fabrics, even in the placed together state, can only be introduced with great difficulty into the corresponding body regions, although they are preferred to spongy elements as a result of their deformability.

The purpose of the present invention is to provide a pad-like implant, which can be successfully used in the treatment of hernias both as regards production and in its provision in sterile form, whilst permitting a high degree of fixation in the initial stage. Since, as is known, these materials cause very limited tissue reactions, it is possible to build up original tissue structures in trouble-free manner.

According to the invention this problem is solved by a pad-like resorbable material, which comprises a closed cushion-like or hose-like body. An outer sleeve comprises a knitted or woven hose of resorbable fiber, which is filled with threads or filaments of resorbable material.

It has surprisingly been found that a cushion-like or hose-like body closed on all sides and whose outer sleeve comprises a knitted or woven hose of resorbable fibres or filaments or a perforated film of resorbable material, which is filled with a filling of threads, filaments, flocks or shreds of the same or another resorbable material, can be used particularly advantageously for the treatment of inguinal and hiatal hernias.

Unlike in the case of the hitherto known multilayer, knitted or woven fabrics or spongy pad materials, the hose or cushion-like body closed on all sides according to the invention and which is filled with resorbable material, offers considerable advantages for the various operative variants for the treatment of hernias. Due to their at least 50% compressibility, the hose-like implant pads can be easily fitted and as a result of their recovery capacity also completely fill the cavities extended during the operation. In addition, the pad-like implants according to the invention can be very adequately fixed, either by sewing to the surrounding tissue or by a ring-like connection of the hose-like body.

A further advantage is that the hose-like outer sleeve can be produced as an endless strip and then, as a function of the desired compressibility and/or recovery capacity, can be filled with threads, filaments, flocks or shreds of different lengths. In addition, the sterilization of an endless hose involves less expenditure and effort than that of individual lobules, which must be placed together by the surgeon shortly before or during the actual operation. The individual hose portions can be made available in a sterile pack and according to a special embodiment of the invention identically or varyingly long hose portions are made available which, as required, are subdivided into the corresponding portions by transverse welds or seams. According to a particularly preferred embodiment, there are also unfilled neutral regions between the transverse seams, which offer the surgeon the possibility of cutting off varyingly long pad-like implants, without exposing the filling. The transverse seams offer the further advantage of better bendability.

As the outer sleeve is preferably made from a weldable material, in the edge regions of the seam are provided more easily resorbable regions. As a result, the polymers are already partly decomposed by the welding, which are consequently more easily resorbable.

It has surprisingly also been found that with the hose-like implants with a fibre filling much better load-bearing tissue structures of partly original tissues form during the resorption of the plastics and they help to contribute to the strengthening of the stomach or diaphragm wall.

As a result of the differing structure of the hose-like outer sleeve and the filling made from fibres, filaments, flocks or shreds, suprisingly neoplasms are obtained, which have only a limited or even no tendency to physiological coalescences.

The use of the pad-like implants according to the invention is mainly in the field of treating inguinal hernias and also in the treatment of axial or paraesophageal hiatal hernias.

Hitherto, up to 20% relapses have had to be expected in the treatment of the inguinal hernia due to the connective tissue and muscle weakness which, even when using the existing tissue for repair purposes, i.e. the closing of the broken hilus, could only be eliminated with limited success, even when additionally using flat pad implants. Hitherto when treating hiatal hernias, particular difficulties have been encountered in reliably fixing the cardia and this led to problems both when using the body's own tissue and the stomach wall in the fundoplication (or with a ligamentum teres used as frenula). Serious complications were also encountered in the case of gel-filled prostheses of non-resorbable silicone sleeves, such as e.g. the Angelchick prosthesis (Akt. Chir 21, 1986, p 132). All the hitherto encountered problems in these fields could be eminently solved by the pad-like, hose-like implants according to the invention, because they reliably fix in dish-like manner and lower esophageal sphincter by forming a load-bearing tissue clamp, the formation of the body's own tissue advancing with increasing resorption of the dish-like structure.

The outer sleeve of the hose-like or cushion-like body can be knitted or woven from fibres or preferably filaments of a resorbable plastic and in particular a polyglactin, working preferably taking place with a small circular knitting or weaving machine. The nature of the knitting pattern or the looping is unimportant. All that is important is that there are small openings in the hose-like sleeve with a diameter of 0.05 to 0.5 mm, in order to permit a passage of tissue fluid and therefore growing in of tissue.

With respect to the structure of the hose filling threads, filaments, flocks or shreds, it must be such that the necessary compressibility and also the desired recovery capacity are ensured. Such a loose thread or flock material in itself gives an adequate penetration possibility for the tissue fluid and therefore for the formation of new tissue.

Through a corresponding choice of the resorbably material of the outer sleeve on the one hand and the filling on the other, the resorption times can be correspondingly set, either when in the case of the pad-like implant a rapid resorption of the filling and therefore an aided formation of scar tissue in the inner hose region is desired, or in that a faster resorbability of the covering from the outside is preferred.

It is also of significance that the easier resorbability occurs at the weld seams, normally transverse seams of the hose-like structure, because the plastics are more decomposed by the welding process and can consequently be more easily resorbed.

It is also possible to produce the outer sleeve in the form of an extrudable hose, which is subsequently e.g. perforated by laser beams and is filled in a further operation with the filling material. Furthermore, the hose can be formed from a fabric or film, which is closed by one or two longitudinal seams.

The invention is described in greater detail hereinafter relative to the drawing, wherein show:

FIG. 1 A perspective view of the implant according to the invention.

Figure 2:
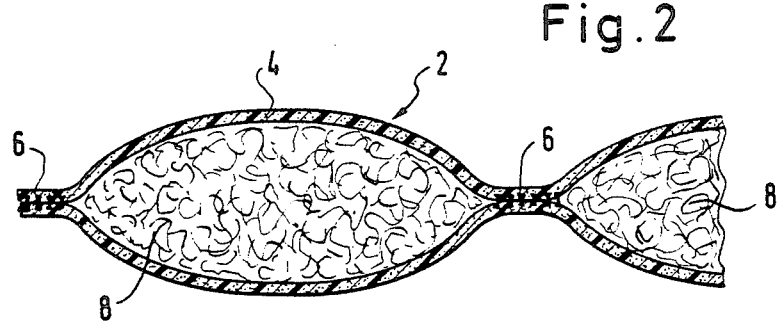

FIG. 2 A longitudinal section through a modified inventive implant.

Figure 3:
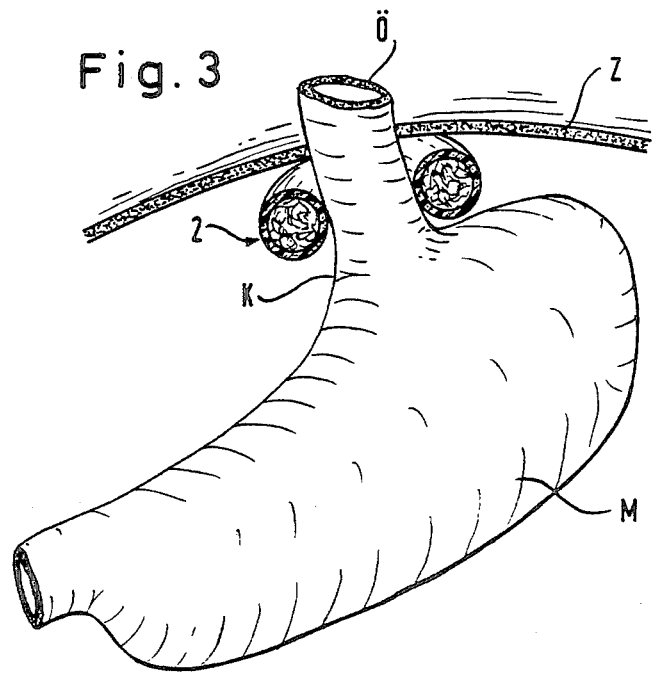

FIG. 3 A diagrammatic drawing of the use of the implant in the case of a hiatal hernia.

In the case of the hose-like implants shown in FIGS. 1 and 2, they comprise an outer sleeve 4 of a resorbable plastic or other porous sheet-like material, which is closed and preferably welded at its end regions 6. End region 6 can be relatively wide and contain a filler-free zone, so that the surgeon can separate the individual hose portions in this neutral region without exposing the filling 8. Filling 8 comprises discrete pieces of individual threads or filaments, preferably 5 to 30 mm long individual threads with a titre of 1 to 20 den. In the case of the diagram of FIG. 3, the pad hose 2 is placed in annular manner around the esophagus O above stomach M and below diaphragm Z in the vicinity of cardia K.

The filling of the hose-like outer sleeve is so dimensioned from the material and volume standpoint, that the implant pad has a compressibility of at least 50%, i.e. by finger pressure it can be compressed at least to half its thickness or is correspondingly deformable. Furthermore, the recovery capacity of the pad-like implant is preferably such that, as a result of the elasticity of the filling material, it has a value of at least 80%. Both the compressibility and the recovery capacity are in the present case related to the "dry" implant, it being assumed that even after inserting the implant and following the penetration of tissue fluid, the compressibility and recovery capacity at least initially remain unchanged.

EXAMPLE

In a roughly 45 year old patient with gastroesophageal reflux, a hose-like pad with a diameter of 12 mm was placed in collar-like manner around the distal esophagus and sewn together at the overlapping ends. There was no further connection to the surrounding tissue. Following a decay time nothing remarkable was endoscopically revealed on the esophagus and stomach, the patient was able to ingest solid food and gained weight. No significant complications were revealed by a barium contrast medium examination. Even after 6 months, no prosthesis displacement could be detected and instead there was a load-bearing, non-coalesced scar formation in the region supported by the implant.

We claim:

1. Pad-like implant of resorbable material for the treatment of hernias, comprising a cushion-like or hose-like body closed on all sides, having an outer enclosing sleeve formed of porous sheet-like material, which is filled with a filling of discrete pieces of resorbable material.

2. Implant pad according to claim 1, wherein the pad has a compressibility of at least 50% and a recovery capacity of at least 80%.

3. Implant pad according to claim 2, wherein said sleeve comprises a weldable outer sleeve of a polyactide, polyglycolide or a p-dioxanone or a copolymer thereof.

4. Implant pad according to claim 3 wherein the filling is of a polylactide, polyglycolide or a p-dioxanone, or a copolymer thereof.

5. Implant pad according to claim 4, wherein the filling comprises 30 to 100 mm long fibres or monofilaments of a resorbable material.

6. Implant pad according to claim 5, wherein the cushion or hose-like body has a diameter of 5 to 25 mm and is subdivided by transverse welds or seams into portions of the same length or into portions of lengths varying between 30 and 80 mm.

7. Implant pad according to claim 6, wherein unfilled neutral regions with a width of 3 to 8 mm are provided between the transverse seams.

8. Implant pad according to claim 1, wherein said porous sheet-like material comprises a knitted hose of resorbable fibres or filaments.

9. Implant pad according to claim 1, wherein said porous sheet-like material comprises a woven hose of resorbable fibres or filaments.

10. Implant pad according to claim 1, wherein said porous sheet-like material comprises a perforated film of resorbable material.

11. Implant pad according to claim 1, wherein said filling comprises threads or filaments of resorbable material.

12. Implant pad according to claim 1, wherein said filling comprises flocks or shreds of resorbable material.

* * * * *